US00PP08930P

United States Patent [19]

Saville

[11] Patent Number: Plant 8,930

[45] Date of Patent: Oct. 11, 1994

[54] MINIATURE ROSE PLANT NAMED SAVASCHOOL

[75] Inventor: F. Harmon Saville, Rowley, Mass.

[73] Assignee: Nor'East Miniature Roses, Inc., Rowley, Mass.

[21] Appl. No.: 148,824

[22] Filed: Nov. 4, 1993

[51] Int. Cl.[5] ..... A01H 5/00

[52] U.S. Cl. ..... Plt./8.2

[58] Field of Search ..... Plt. 8.2

*Primary Examiner*—Howard J. Locker

*Attorney, Agent, or Firm*—Christie, Parker & Hale

[57] ABSTRACT

A new miniature rose with yellow flowers of good form.

1 Drawing Sheet

SUMMARY OF THE INVENTION

The present invention relates to a new and distinct variety of rose plant of the miniature rose class, which was created by me by crossing as seed parent the variety known as 'Klima' and as pollen parent the variety known as 'Sonnenkind'. The varietal denomination of this new rose is 'Savaschool'.

Among the novel characteristics possessed by this new variety which distinguishes it from its parents and all other varieties of which I am aware is its attractive yellow flowers of good form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Klima'.

*Pollen parent.*—'Sonnenkind'.

Class: Miniature.

The following observations were made of specimens grown under glass in Essex County, Mass., during the month of September.

FLOWER

Blooming habit: Recurrent, continuous.

A. Bud:

(1) *Size.*—Medium.

(2) *Form.*—Ovate.

(3) *Color.*—As sepals divide, bud color is near 11B to 13D.

(4) *Sepals.*—Slightly longer than bud, sparsely foliated.

(5) *Peduncle.*—Length — about 1⅛ inches. Aspect — straight. Strength — erect. Color — near 144B.

B. Bloom:

(1) *Size.*—Average size when fully expanded — about 1¾ inches.

(2) Borne.— Singly.

(3) *Form.— High centered at first becoming flat, petals at first loosely rolled under then becoming quilled at maturity.*

(4) *Petalage.*—Number of petals under normal conditions — about 43–45.

(5) *Color.*—During first two days, inner petals at center of flower near 16B; outer petals near 16D; base of petals at point of attachment near 9A; reverse of petals near 16D to 9D and general tonality from a distance bright canary yellow. As bloom ages the attractive yellow color remains but the general tonality gets lighter.

C. Petals:

(1) *Texture.— Thick.*

(2) *Appearance.*—Inside velvety and outside satiny.

(3) *Form.*—Rounded fan shape, slight point at apex.

(4) *Arrangement.*—Imbricated, regularly arranged, shingle-like.

(5) *Petaloids in center.*—Few.

(6) *Persistence.*—Drop off cleanly.

(7) *Fragrance.*—None.

(8) *Lasting quality.*—Average.

REPRODUCTIVE ORGANS

A. Stamens, filaments and anthers:

*Arrangement and color.*—Regularly arranged around styles; color — near 17C.

B. Pollen:

*Color.*—Near 17B.

C. Styles: Uneven length, thin.

D. Stigmas:

*Color.*—Near 2D.

E. Hips: None observed.

PLANT

A. Form: Compact.

B. Growth: Very vigorous, uniform branching; height attained about 14–18 inches.

C. Foliage: Compound 5 to 7 leaflets.

(1) *Size.*—Medium.

(2) *Quantity.*—Abundant.

(3) *Color.*—New foliage: Upper side — near 143A. Underside — near 143B. Old foliage: Upper side — near 137A. Underside — near 138B.

(4) *Shape.*—Oval, pointed.

(5) *Texture.*—Upper side is semi-glossy; underside is matte.

(6) *Edge.*—Serrated.

(7) *Serration.*—Shallow.

(8) *Leaf stem.*—Color — near 143A. Underside — 143B.

(9) *Stipules.*—Medium length, slightly bearded.

(10) *Resistance to disease.*—Blackspot — average. Mildew — average. Rust — average.

D. Wood:

(1) *New wood.*—Color — near 143A. Bark — smooth.

(2) *Old wood.*—Color — near 143B. Bark — rough.

E. Thorns:

(1) *Thorns.*—Quantity (main stalk) — few. On laterals from stalk — very few. Form — short, thin, straight pointed. Length — short. Color — near 184C. Position — irregular.

(2) *Prickles.*—None.

F. Winter hardiness: Needs protection in severe climates.

I claim:

1. A new and distinct variety of rose plant of the miniature rose class, substantially as shown and described.

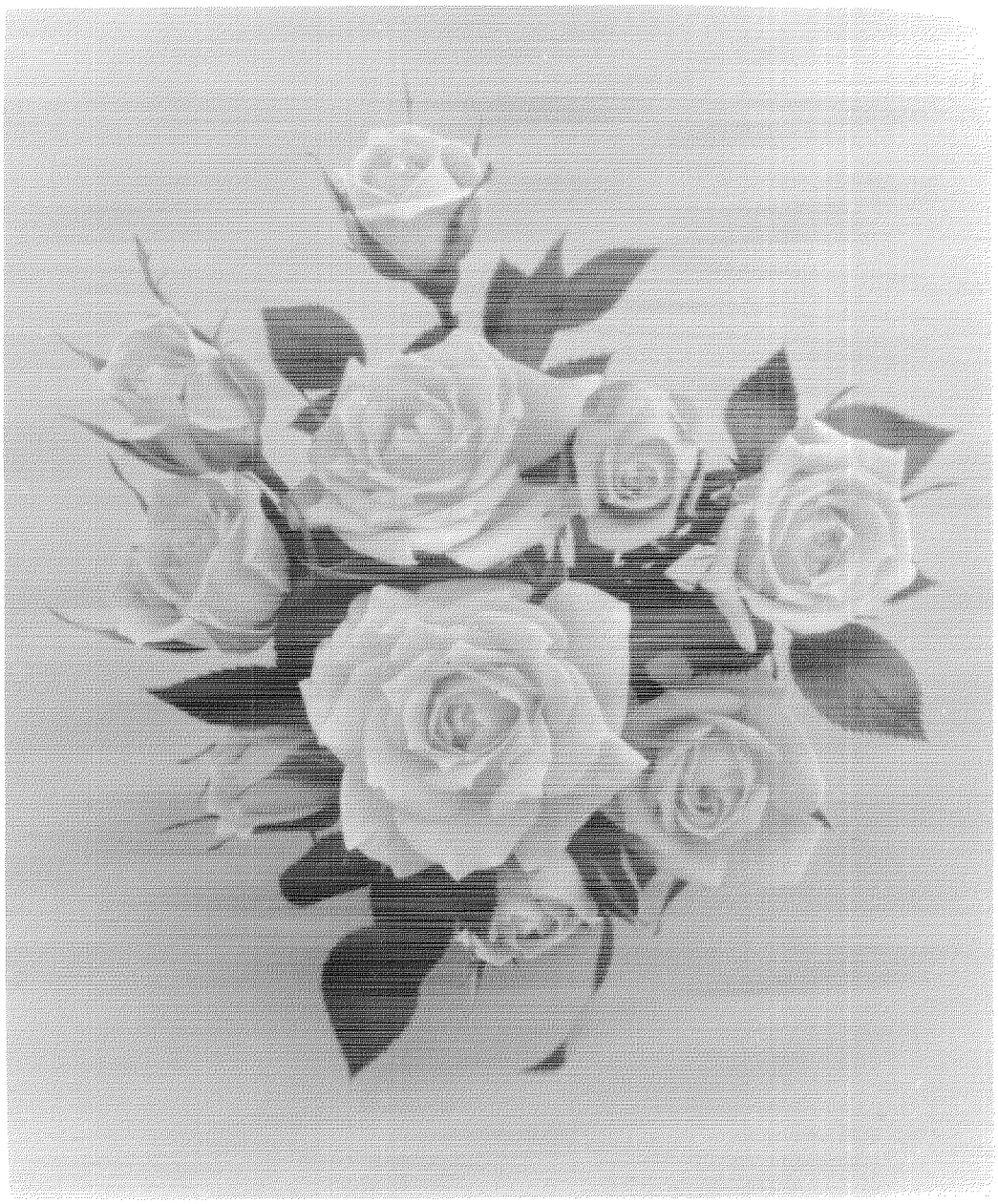

* * * * *